(12) United States Patent
Young et al.

(10) Patent No.: US 7,287,319 B2
(45) Date of Patent: Oct. 30, 2007

(54) METHOD OF MAKING A HOUSING FOR DRUG DELIVERY

(75) Inventors: Wendy A. Young, San Jose, CA (US); Lothar W. Kleiner, Los Altos, CA (US)

(73) Assignee: ALZA Corporation, Mountain View, CA (US)

( * ) Notice: Subject to any disclaimer, the term of this patent is extended or adjusted under 35 U.S.C. 154(b) by 235 days.

(21) Appl. No.: 11/101,844

(22) Filed: Apr. 7, 2005

(65) Prior Publication Data

US 2005/0193554 A1 Sep. 8, 2005

Related U.S. Application Data

(63) Continuation of application No. 10/324,279, filed on Dec. 19, 2002, now Pat. No. 7,024,762.

(60) Provisional application No. 60/343,003, filed on Dec. 19, 2001.

(51) Int. Cl.
*H01R 43/00* (2006.01)
(52) U.S. Cl. .............................. 29/825; 29/874; 604/20
(58) Field of Classification Search .................. 29/825, 29/874; 604/20
See application file for complete search history.

(56) References Cited

U.S. PATENT DOCUMENTS

| | | | |
|---|---|---|---|
| 4,063,352 A | 12/1977 | Bevilacqua | |
| 4,141,359 A | 2/1979 | Jacobsen et al. | |
| 4,365,634 A * | 12/1982 | Bare et al. | 600/391 |
| 4,383,529 A | 5/1983 | Webster | |
| 4,409,981 A | 10/1983 | Lundberg | |
| 4,441,500 A | 4/1984 | Sessions et al. | |
| 4,640,289 A | 2/1987 | Craighead | |
| 4,731,926 A | 3/1988 | Sibalis | |
| 4,856,188 A | 8/1989 | Sibalis | |
| 5,006,108 A | 4/1991 | LaPrade | |
| 5,047,007 A | 9/1991 | McNichols et al. | |
| 5,158,537 A | 10/1992 | Haak et al. | |
| 5,167,617 A | 12/1992 | Sibalis | |
| 5,224,927 A | 7/1993 | Tapper | |
| 5,224,928 A | 7/1993 | Sibalis et al. | |
| 5,246,418 A | 9/1993 | Haynes et al. | |
| 5,254,081 A | 10/1993 | Maurer et al. | |
| 5,288,289 A | 2/1994 | Haak et al. | |
| 5,310,404 A * | 5/1994 | Gyory et al. | 604/20 |
| 5,320,598 A | 6/1994 | Haak et al. | |
| 5,380,272 A | 1/1995 | Gross | |
| 5,582,587 A | 12/1996 | Gyory et al. | |
| 5,612,513 A | 3/1997 | Tuttle et al. | |
| 5,653,682 A | 8/1997 | Sibalis | |

(Continued)

FOREIGN PATENT DOCUMENTS

WO WO-02/41038 7/2003

OTHER PUBLICATIONS

International Search Report for PCT/US02/41038.

*Primary Examiner*—Carl J. Arbes
(74) *Attorney, Agent, or Firm*—Scott S. Servilla; Diehl Servilla LLC

(57) ABSTRACT

An electrotransport reservoir housing which contains, integrally formed therein, at least one region of conductive material which allows for a liquid and moisture tight barrier, while at the same time providing a means for conducting an electric current therethrough.

13 Claims, 5 Drawing Sheets

U.S. PATENT DOCUMENTS

| | | |
|---|---|---|
| 5,907,477 A | 5/1999 | Tuttle et al. |
| 5,976,101 A * | 11/1999 | Sibalis ........................ 604/20 |
| 5,995,869 A * | 11/1999 | Cormier et al. ............... 604/20 |
| 6,163,720 A | 12/2000 | Gyory et al. |
| 6,181,963 B1 | 1/2001 | Chin et al. |
| 6,233,471 B1 | 5/2001 | Berner et al. |
| 7,024,762 B2 * | 4/2006 | Young et al. ................. 29/825 |

* cited by examiner

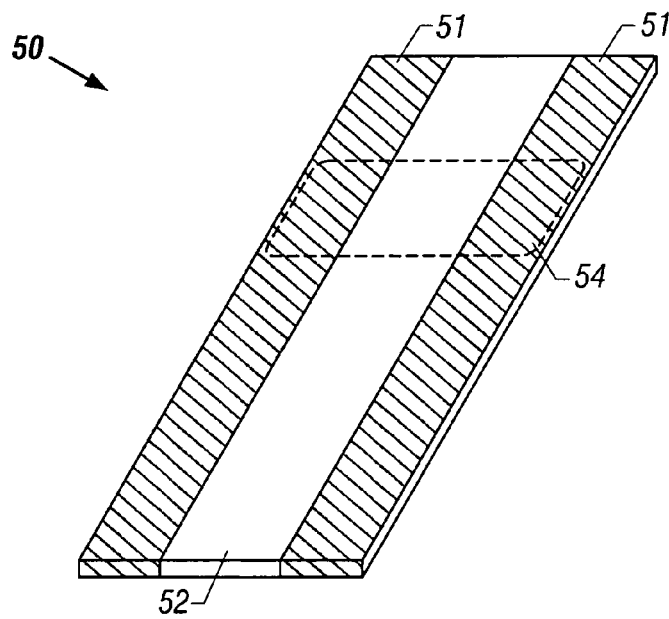
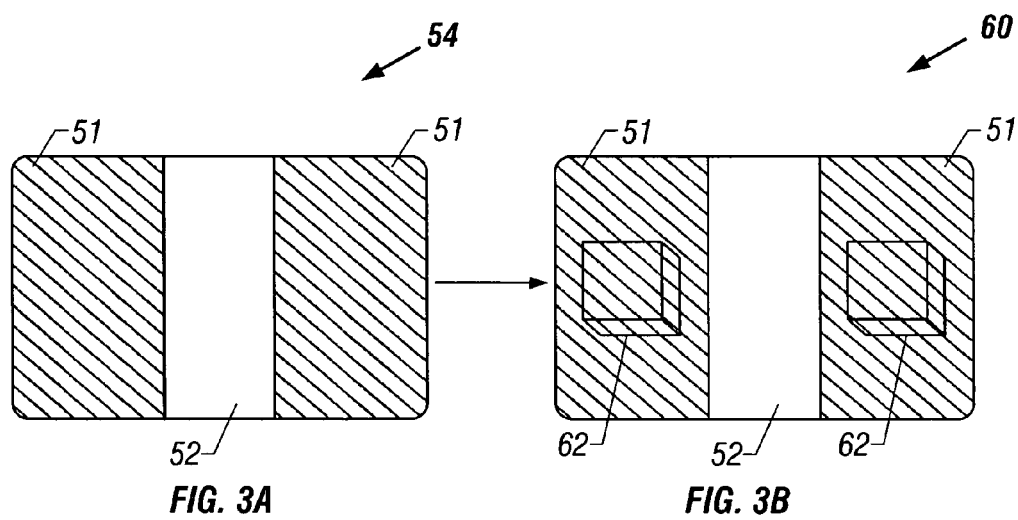

METHOD OF MAKING A HOUSING FOR DRUG DELIVERY

CROSS REFERENCE TO RELATED U.S. APPLICATION DATA

The present application is a continuation application of application Ser. No. 10/324,279, filed Dec. 19, 2002, now U.S. Pat. No. 7,024,762 which claimed priority benefits of provisional application 60/343,003, filed Dec. 19, 2001.

TECHNICAL FIELD

The present invention relates to a transdermal agent delivery and sampling device having a reservoir housing which can be thermoformed in one embodiment from material having a nonconductive center strip located between two conductive strips. A reservoir housing fabricated in this manner results in a single integral piece having two gel reservoir cavities thermoformed at each end from the conductive outer strips and an insulating barrier located between the cavities which was formed from the nonconductive center strip. Utilization of such a housing allows for current to be transmitted through each electrically conductive housings without the need to drill holes through non-conductive cavities and then attempt to seal those holes during final assembly.

BACKGROUND ART

The term "electrotransport" refers generally to the delivery or extraction of an agent (charged, uncharged, or mixtures thereof) through a body surface (such as skin, mucous membrane, or nails) wherein the delivery or extraction is at least partially electrically induced or aided by the application of an electric potential. The electrotransport process has been found to be useful in the transdermal administration of many drugs including lidocaine, hydrocortisone, fluoride, penicillin, and dexamethasone. A common use of electrotransport is in diagnosing cystic fibrosis by delivering pilocarpine iontophoretically. The pilocarpine stimulates production of sweat. The sweat is then collected and analyzed for its chloride content to detect the presence of the disease. Electrotransport devices generally employ two electrodes, positioned in intimate contact with some portion of the animal's body (e.g., the skin). A first electrode, called the active or donor electrode, delivers the therapeutic agent (e.g., a drug) into the body. The second electrode, called the counter or return electrode, closes an electrical circuit with the first electrode through the animal's body. A source of electrical energy, such as a battery, supplies electric current to the body through the electrodes. For example, if the therapeutic agent to be delivered into the body is positively charged (i.e., cationic), the anode is the active electrode and the cathode is the counter electrode to complete the circuit. If the therapeutic agent to be delivered is negatively charged (i.e., anionic), the cathode is the donor electrode and the anode is the counter electrode.

A widely used electrotransport process, electromigration (also called iontophoresis), involves the electrically induced transport of charged ions (e.g., drug ions) through a body surface. Another type of electrotransport, called electroosmosis, involves the trans-body surface (e.g., transdermal) flow of a liquid under the influence of the applied electric field. Still another type of electrotransport process, called electroporation, involves forming transiently existing pores in a biological membrane by applying high voltage pulses. In any given electrotransport system, one or more of these processes may occur simultaneously to some extent.

Most transdermal electrotransport devices have an anodic and a cathodic electrode assembly, each electrode assembly being comprised of an electrically conductive electrode in ion-transmitting relation with an ionically conductive liquid reservoir which in use is placed in contact with the patient's skin. Gel reservoirs such as those described in Webster U.S. Pat. No. 4,383,529 are the preferred form of reservoir since hydrated gels are easier to handle and manufacture than liquid-filled containers. Water is by far the preferred liquid solvent used in such reservoirs, in part because many drug salts are water-soluble and in part because water has excellent biocompatability, making prolonged contact between the hydrogel reservoir and the skin acceptable from an irritation standpoint.

The term "agent" is intended to have its broadest interpretation and is used to include any therapeutic agent or drug, as well as any body analyte, such as glucose. The terms "drug" and "therapeutic agent" are used interchangeably to refer to any therapeutically active substance that is delivered to a living organism to produce a desired, usually beneficial, effect. This includes therapeutic agents in all the major therapeutic areas including, but not limited to: anti-infectives such as antibiotics and antiviral agents; analgesics, including fentanyl, sufentanil, buprenorphine and analgesic combinations; anesthetics; anorexics; antiarthritics; anti-asthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anti-cholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

Of particular interest in transdermal delivery is the delivery of analgesic drugs for the management of moderate to severe pain. Control of the rate and duration of drug delivery is particularly important for transdermal delivery of analgesic drugs to avoid the potential risk of overdose and the discomfort of an insufficient dosage. One class of analgesics that has found application in a transdermal delivery route is the synthetic opiates, a group of 4-aniline piperidines. These synthetic opiates, e.g., fentanyl and certain of its derivatives such as sufentanil and remifentanil, are particularly well-suited for transdermal administration. These synthetic opiates are characterized by their rapid onset of analgesia, high potency, and short duration of action. They are estimated to be 80 times (fentanyl) and 800 times (sufentanil), more potent than morphine. These drugs are weak bases, i.e., amines, which are primarily cationic in acidic media.

Electrotransport devices use at least two electrodes, an anode and a cathode, that are in electrical contact with some portion of the skin, nails, mucous membrane, or other surface of the body. One electrode, commonly called the "donor" electrode, is the electrode which is used to deliver the agent into the body. The other electrode, typically termed the "counter" electrode, serves to close the electrical circuit through the body. For example, if the agent to be delivered is positively charged, i.e., a cation, then the anode is the donor electrode, while the cathode is the counter electrode which serves to complete the circuit. Alternatively, if an agent is negatively charged, i.e., an anion, the cathode is the donor electrode and the anode is the counter electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a biocompatible electrolyte salt. The power supply unit has electrical controls for adjusting the amount of electrical current applied through the electrodes. The "satellite" electrodes are connected to the electrical power supply unit by long (e.g., 1-2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al., U.S. Pat. No. 4,141,359 (see FIGS. 3 and 4); LaPrade, U.S. Pat. No. 5,006,108 (see FIG. 9); and Maurer et al., U.S. Pat. No. 5,254,081.

More recently, electrotransport delivery devices have become much smaller, particularly with the development of miniaturized electrical circuits (e.g., integrated circuits) and more powerful light weight batteries (e.g., lithium batteries). The advent of inexpensive miniaturized electronic circuitry and compact, high-energy batteries has meant that the entire device can be made small enough to be unobtrusively worn on the skin of the patient, under clothing. This allows the patient to remain fully ambulatory and able to perform all normal activities, even during periods when the electrotransport device is actively delivering drug. Such small self-contained electrotransport delivery devices are disclosed for example in Tapper, U.S. Pat. No. 5,224,927; Sibalis, et al., U.S. Pat. No. 5,224,928; and Haynes et al., U.S. Pat. No. 5,246,418.

Reference is now made to FIG. 1 which depicts an exploded view of an exemplary electrotransport device 10 having an activation switch in the form of a push button switch 12 and a display in the form of a light emitting diode (LED) 14. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is generally composed of rubber or other elastomeric material, such as an ethylene vinyl acetate copolymer having 28% vinyl acetate (EVA-28). Lower housing 20 is typically composed of a plastic or elastomeric sheet material (such as, e.g., polyethylene terephthalate glycol (PETG) or polyethylene) which can be easily molded or thermoformed to form cavities and is then cut to form openings therein. Printed circuit board assembly 18 comprises an integrated circuit 19 coupled to discrete electrical components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

On the underside of circuit board assembly 18 is a battery 32, which may be a button cell battery, such as a lithium cell. The circuit outputs of the circuit board assembly 18 make electrical contact with the electrodes 24 and 22 through openings 23, 23' in the cavities 25, 25' formed in lower housing, by means of electrically conductive adhesive strips 42, 42'. Electrodes 22 and 24, in turn, are in direct mechanical and electrical contact with the top sides 44', 44 of drug reservoir 26 and electrolyte reservoir 28. The bottom sides 46', 46 of reservoirs 26,28 contact the patient's skin through the openings 29',29 in adhesive 30. Upon depression of push button switch 12, the electronic circuitry on circuit board assembly 18 delivers a predetermined DC current to the electrodes/reservoirs 22,26 and 24,28 for a delivery interval of predetermined length.

Electrotransport delivery devices are prepared, shipped and stored (or stored, shipped and stored), prescribed and then used. As a result, the devices must have components that have extended shelf lives that, in some instances, must comply with regulatory requirements. For instance, the U.S. Food and Drug Administration has shelf life requirements of from six to eighteen months for some materials. One complicating factor in achieving an extended shelf life is the dimensional stability of EVA-28 when exposed to elevated temperatures. In order to achieve satisfactory dimensional stability of the device housing when it is manufactured from EVA-28, for example, the molding conditions must be carefully optimized, thus limiting the processing window. Otherwise warpage as well as unacceptable dimensional changes will occur at temperatures as low as 40□C. If the device housing should encounter excessive heat during storage or shipping, however, these same undesirable dimensional changes can occur. Further, electrotransport delivery devices typically contain electronic components (e.g., integrated circuits), conductive circuit traces and electrical connections therebetween which can corrode or otherwise be degraded by water or water vapor. Unfortunately, devices such as device 10 shown in FIG. 1 have hydratable or hydrated reservoirs 26, 28. Thus, humidity or moisture from the hydrated reservoirs can permeate through the device housing during manufacturing and storage, which can thus cause corrosion of the electronic components within the device, thereby reducing the shelf life of the device. One source of permeation is around the electrical leads or contacts which must supply electric current and voltage from the battery into the relatively wet environment of the reservoir housing.

In order to apply voltage from a power source to the agent reservoir, there must be some method or device used to place the power source in electrical communication with the drug reservoir.

One method is to mold or punch a hole in the plastic housing used to contain the reservoir gel. An electrode is then placed on the outside of the housing covering the hole. The gel is then placed within the reservoir cavity so that electrical contact can be made with the electrode through the hole in the housing.

There are several critical points in the implementation of this method. All of which involve sealing the hole in the reservoir housing. Because the reservoirs gels are largely water, liquid and/or moisture can escape from housing and corrode the electronic components if there is not proper sealing between the electrode and the housing and the housing and the gel and the housing. Because these devices are shipped and stored in sealed pouches, any moisture leaking from the reservoir may get trapped in the interior of the device and expose the controller circuitry to the water. Water, particularly water containing electrolyte salts such as found in a reservoir gel, can be very corrosive and quite damaging to the device.

One solution has been to develop dry or non-hydrated electrodes. See for example U.S. Pat. Nos. 5,158,537; 5,288,289; 5,310,404; and 5,320,598. Because the gel matrix only needs to be hydrated during actual use by the patient during drug delivery, the device can be manufactured and stored with the reservoir in a dry or non-hydrated state. Then a hydrating liquid, with or without the agent to be delivered contained within the liquid, is added to the reservoir just prior to use. But this approach is not without its own engineering challenges.

Another approach has been to make the device resistant to the moisture and corrosion. One step that has been taken to combat the corrosion problem has include gold plating the contact tabs and circuit board traces. Such solutions are inherently expensive and add additional steps to the manufacturing process.

DESCRIPTION OF THE INVENTION

The present invention provides an electrotransport reservoir housing formed from a single piece of material having at least two conductive sections and at least one non-conductive section. This material can be formed by co-extruding a non-conductive strip located between two conductive strips. A reservoir blank, which is a section of the appropriate size, is punched across the extruded material such that a conductive region is located at each end of the piece and the non-conductive section is in the middle of the piece, between the two conducive regions. This reservoir blank is then thermoformed to fabricate an integral reservoir housing having two cavities, one at each end of the piece. Each cavity is formed from one of the two conductive regions and the two cavities are separated and insulated from each other by the section of non-conductive material.

Once extruded, the three part material is thermoformed into a reservoir housing which functions as an integral sheet of material which, even after having been thermoformed, provides a liquid and moisture tight housing while at the same time, providing a means to pass electric current through the housing. This results in a reservoir housing that is essentially a single integral component with no holes or other passages through the housing which would require sealing. By having each cavity at least partially molded from conductive material, problems of leakage of liquid and/or moisture from the reservoir gel which will be inserted therein are eliminated.

BRIEF DESCRIPTION OF THE DRAWINGS

A better understanding of the present invention as well as other objects and advantages thereof will become apparent upon consideration of the following detailed description especially when taken with the accompanying drawings, wherein like numerals designate like parts throughout, and wherein:

FIG. 2 is a perspective view of a three part co-extruded sheet;

FIGS. 3A and 3B are a schematic views of the patch of material punched from the co-extruded sheet and the final thermoformed reservoir housing;

MODES FOR CARRYING OUT THE INVENTION

Figure 1:
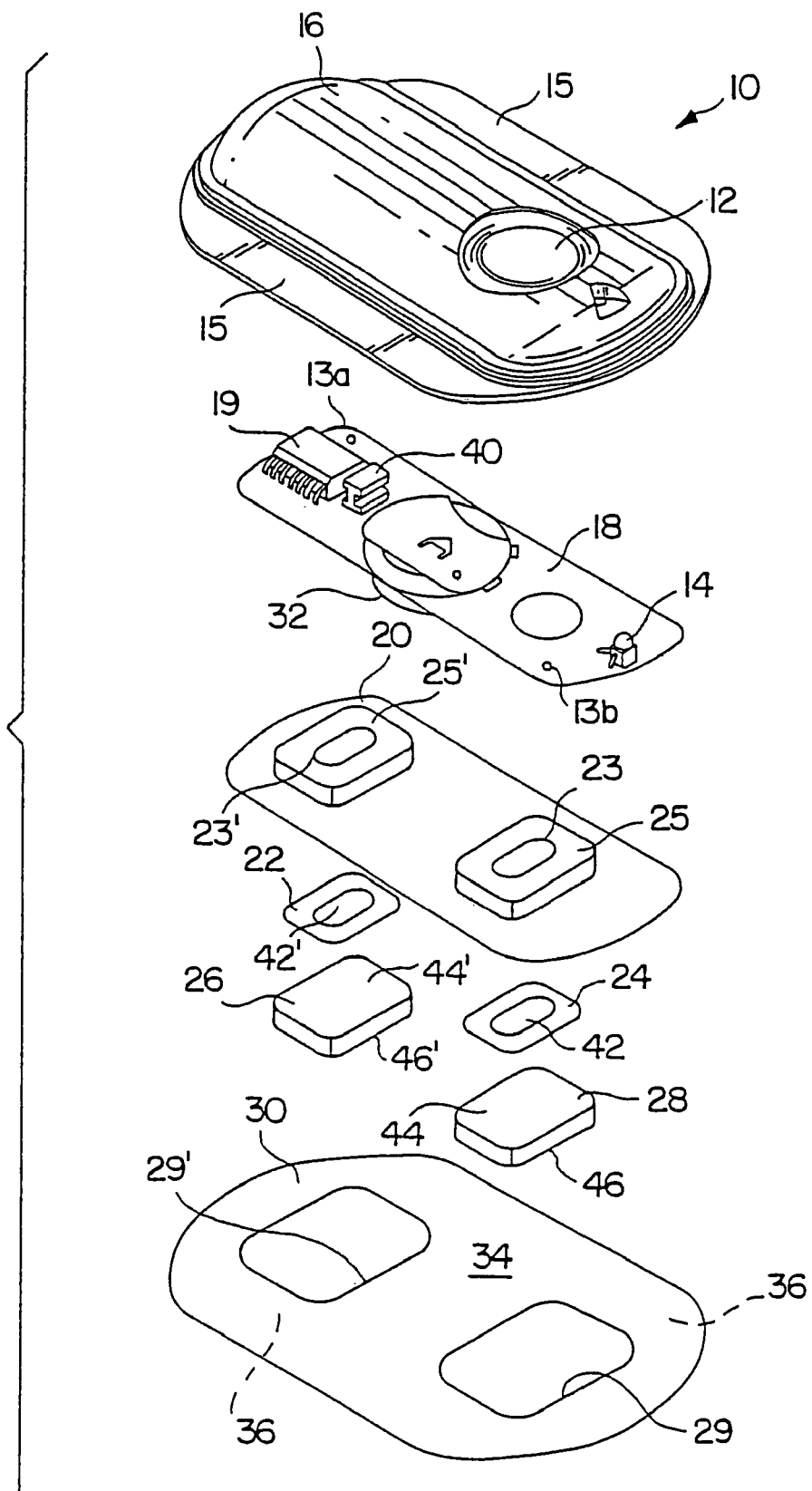
FIG. 1 is a perspective view of a generic electrotransport device.

Reference is now made to the drawings in detail and in particular FIG. 2. Sheet 50 is made up of two strips of Conductive Strip 51 and one strip of Non-Conductive Strip 52. As shown here in FIG. 2 and in all other figures herein, conductive regions are shown hatched and non-conductive regions are not hatched.

There are several ways in which Sheet 50 can be manufactured. One way is to start with preformed strips of Conductive Strip 51 and Non-Conductive Strip 52, which are typically formed by extrusion. These strips are laid side-by-side lengthwise and then placed so that they overlap one or more of the other strips. The overlapping strips are then calendered, under the right conditions, to a predetermined thickness which fuses the overlapping layers. The process can be done step wise. First, fusing/calendering two of the strips together and then overlapping and calendering the third. Alternatively, it is possible to overlap all three and fuse/calender them at one time. In either case, the result is the formation of Sheet 50. The steps and parameters for performing the calendaring are known in the art or easily determined by one skilled in the art.

An alternative is to co-extrude the conductive and non-conductive materials. One way this can be accomplished is by having three separate extruders, one for each strip, which feed into a special three-into-one die, typically called a co-extrusion die. The output of the die is the composite Strip 50 as shown in FIG. 2.

A more likely variation would be to have one extruder for the conductive material and one extruder for the non-conductive material. As the conductive material exits the extruder, it is split into two strips and a second extruder, containing the non-conductive material, extrudes a non-conductive strip between the two conductive strips which also results in the formation of Sheet 50. This method is usually accomplished by feeding both extruders into one special die which is designed to handle the required functions. Other methods of manufacture are known to those skilled in the art.

The extrusion/calendering processes result in the material being formed to the proper thickness, which is typically in the range of 3 mils to 20 mils thick. The preformed strips of Conductive Strip 51 and Non-conductive Strip 52 are typically in range of 0.125 inches to 2 inches wide. Likewise, if Sheet 50 is formed by a co-extrusion process, the regions of conductive and non-conductive material are typically in the range of 0.125 inches to 2 inches wide. However, the width of these regions could certainly be larger or smaller based upon other engineering and product design requirements. The steps and parameters for performing the extrusions are known in the art or easily determined by one skilled in the art.

The conductive material could be any material which can be compounded with carbon black and subsequently co-extruded and thermoformed. Such materials include without limitation polyvinyl chloride (PVC), polyethylene terephthalate glycol (PETG), polyethylene (PE), polypropylene (PP), polycarbonate (PC), acrylics, and similar materials. The range of resistivity suitable for the conductive polymer is less than about 10,000 ohms-cm, which could be achieved by compounding the polymer with at least about 3 vol % of various carbon blacks. The actual volume percent of carbon black depends upon both the grade of the carbon black and target resistivity of the particular material being produced. The non-conductive material should have a resistivity of about $10^9$ ohms-cm or greater. The conductive and non-conductive material could be extruded in an C—N—C pattern (where C is conductive and N is non-conductive), or if thinner areas of conductive material are desired, in a N—C—N—C—N pattern as described below in FIG. 4.

A portion of Sheet 50 is then separated from the Sheet 50 to form a Reservoir Blank 54. The separation is usually accomplished by way of a punch press, die cutting or other standard fabrication techniques. The separation is generally made across the width of Sheet 50 so that the material that is removed contains material from all three strips, two conductive and one non-conductive, that were used to produce Sheet 50. Reservoir Blank 54 is shown as a dotted line in FIG. 2 to indicated the outline of where Sheet 50 would be punched or cut in order to produce Reservoir Blank 54.

Figure 4:
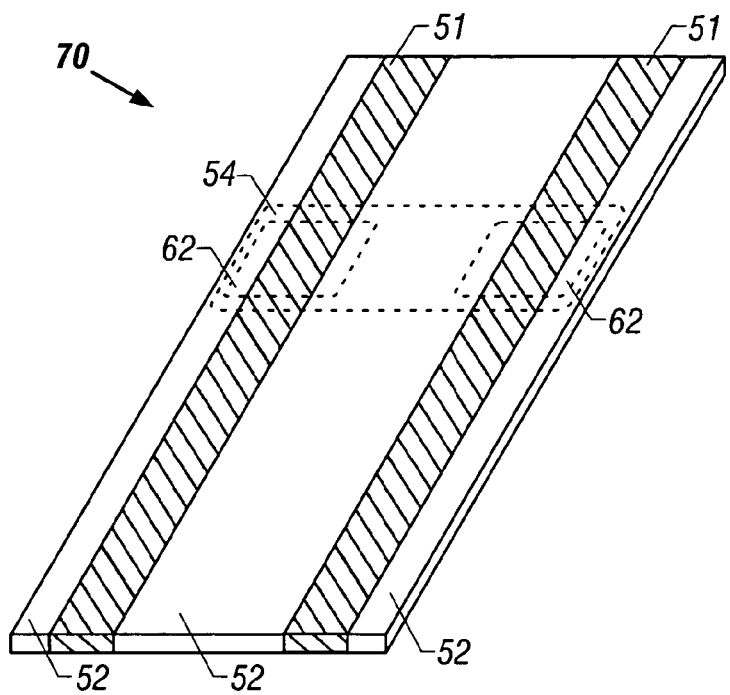
FIG. 4 is a perspective view of a five part co-extruded sheet.

Sheet 50 can be produced in several sizes. It might be large enough to accommodate several Reservoir Blanks 54 as shown in FIG. 2 and FIG. 4. It also could be made in a much longer continuous ribbon that could accommodate a multiplicity of Lower Housing Blanks. In the alternative, it could be sized to be slightly larger than or exactly the same size as the Reservoir Blank 54.

FIG. 3A shows Reservoir Blank 54 that has been separated from Sheet 50. Reservoir Blank 54, in this embodiment, is comprised of two to outer regions of Conductive Strip 51 and the middle Non-conductive Strip 52. FIG. 3B shows Lower Housing 60 after Reservoir Blank 54 has been subjected to a thermoforming process which heats Reservoir Blank 54 and causes the heated Reservoir Blank 54 to conform to the shape of a mold by the application of a vacuum to the heat-softened Reservoir Blank 54. The thermoforming process forms the two Reservoir Cavities 62.

The two sections of Conducting Strip 51 are typically black in color because they contain carbon black which is used in order to impart the conductivity characteristic. However, the middle Non-Conductive Strip 52 could be any of a number of colors that are readily available to those familiar with the art.

FIG. 4 shows a Co-Extruded Sheet 70 which is similar to the Sheet 50 of FIG. 2, except that it is formed from five strips of material. Each outer Non-conducting Strip 52 and the center Non-conducting Strip 52 are non-conductive and the two remaining Conductive Strips 51 are conductive. The area which would be separated from Co-extruded Sheet 70 to form Reservoir Blank 54 is shown in outline form. The areas of Reservoir Blank 54 which will be formed into Reservoir Cavities 62 are also shown in outline form.

Figure 5:
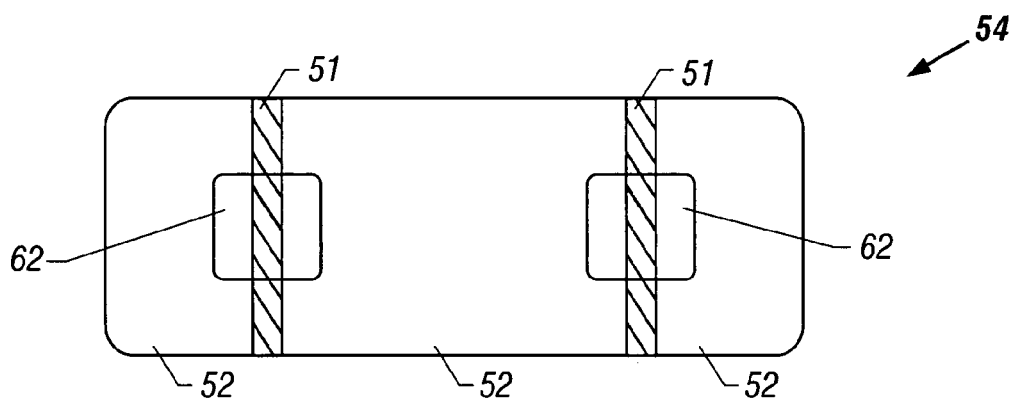
FIGS. 5 and 6 are perspective views of two variations of lower housings thermoformed from a five-part extruded sheet.
Figure 6:
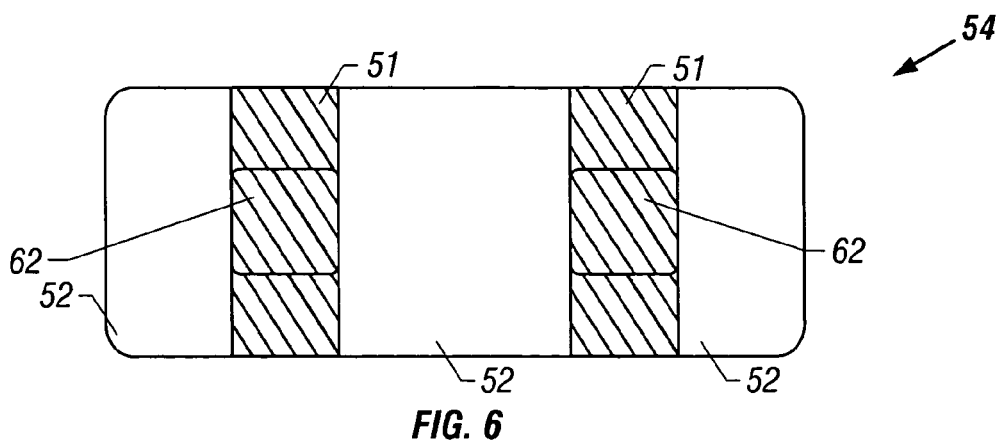

This five part configuration for Co-extruded Sheet 70 permits the width of the Conductive Strips 51 and Non-conductive Strips 52 to be varied according to various design requirements. FIG. 5 and FIG. 6 each show a variation of Reservoir Blank 54 made from two different 5-part Co-extruded Sheet 70. The Conductive Strips 51 could be narrow as in FIG. 5, in which the Conductive Strip 51 comprises a portion of Reservoir Cavity 62. Conductive Strips 51 could also be wider comprising almost all of Reservoir Cavity 62 as shown in FIG. 6.

Figure 7:
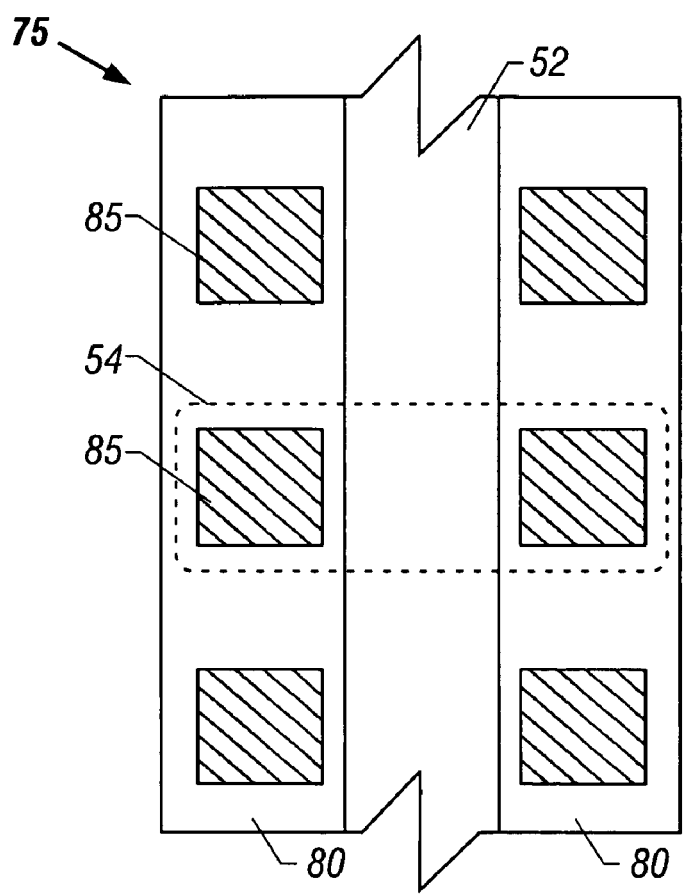
FIG. 7 is a schematic view of a three-part extruded system having patches of conductive material incorporated into the two outer strips.

Another embodiment is shown in FIG. 7. In this embodiment, Co-extruded Sheet 75 is made from a modified form of Conductive Strip 51. This modified form is Non-contiguous Conductive Strip 80. This strip is comprised of largely non-conductive material having embedded therein, smaller regions of conductive material forming one or more Conductive Patches 85. The region that would be separated from Co-extruded Sheet 75 and would become Reservoir Blank 54 is shown in outline form. Reservoir Blank 54 is then subjected to thermoforming which would cause the formation of Reservoir Cavities 62.

Figure 8:
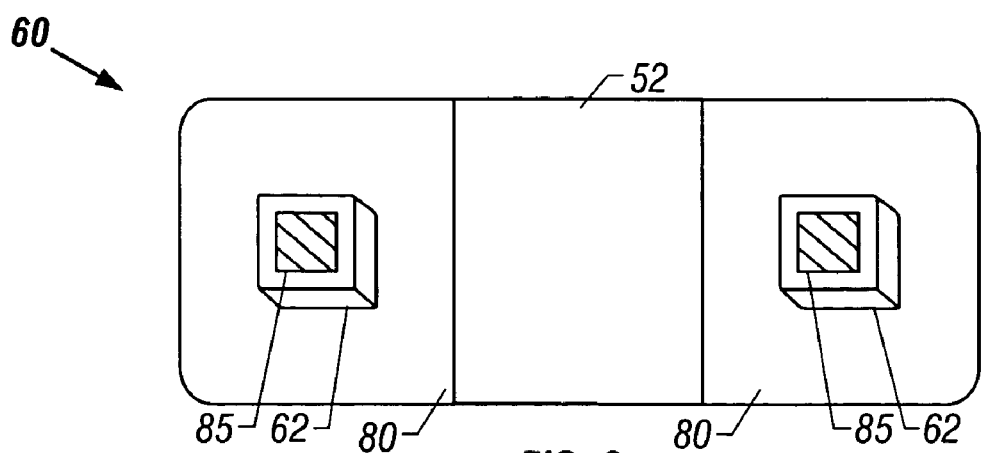
FIGS. 8, 9, 10 and 11 are perspective views of four variations of lower housings thermoformed from a five-part extruded starting material having patches of conductive material incorporated in the outer two strips.
Figure 9:
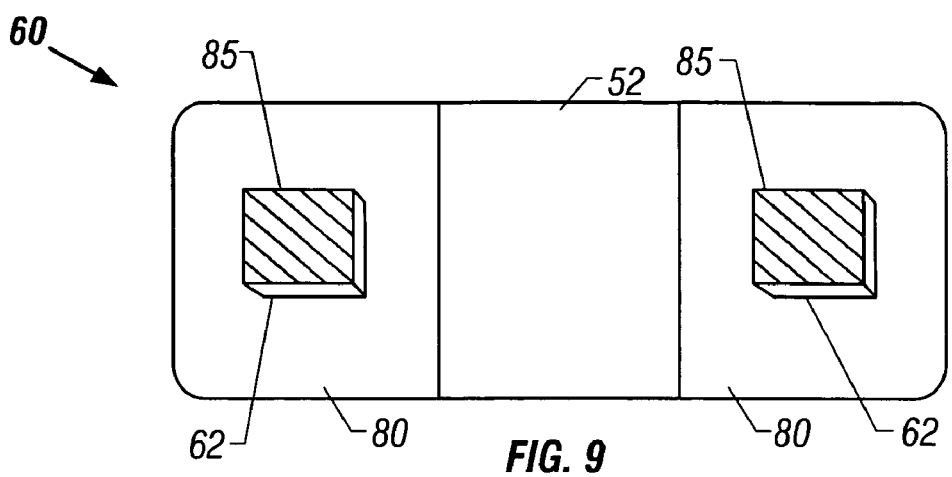
Figure 10:
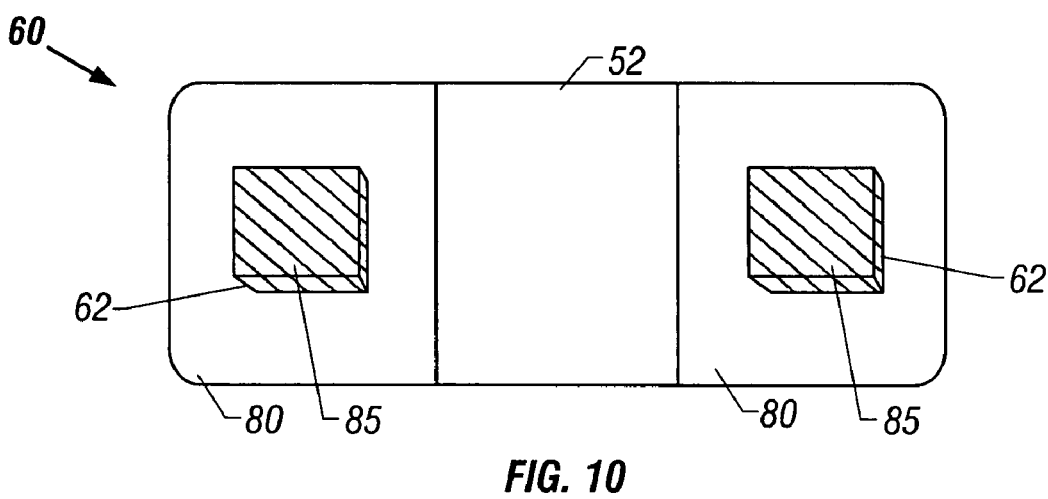
Figure 11:
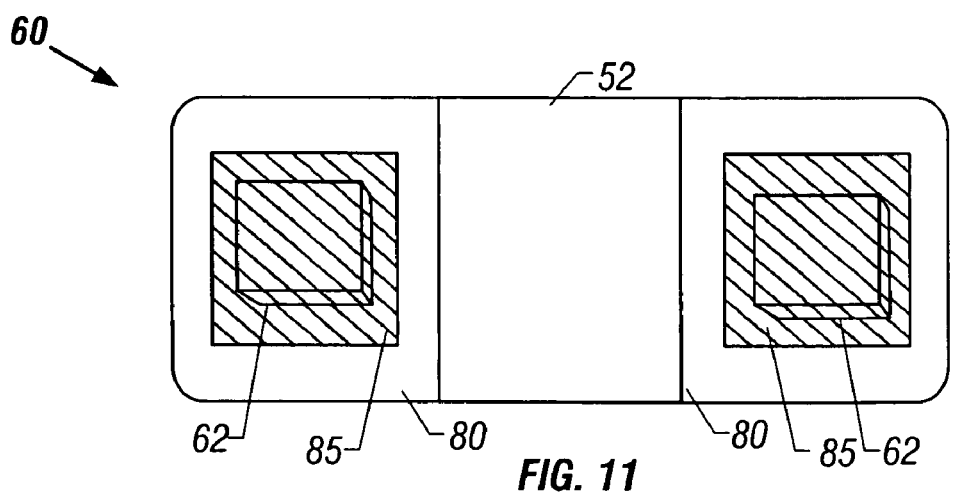

Conductive Patch 85 might be sized in relation to Reservoir Cavity 62 such that some portion of the bottom of Reservoir Cavity 62 was non-conductive (FIG. 8). Conductive Patch 85 could also be sized in relation to Reservoir Cavity 62 such that the entire bottom of Reservoir Cavity 62 would be comprised of Conductive Patch 85 (FIG. 9). Similarly Conductive Patch 85 might be sized in relation to Reservoir Cavity 62 so that Conductive patch 85 covers all of the bottom of Reservoir Cavity 62 as well as some of the side walls of Reservoir Cavity 62 (FIG. 10). Finally, Conductive Patch 85 might be sized in relation to Reservoir Cavity 62 so that Conductive patch 85 covers all of the bottom of Reservoir Cavity 62, the side walls of Reservoir Cavity 62 and as well as some of the planer surface of Reservoir Blank 54 (FIG. 11).

Though the embodiments shown herein describe the formation of reservoir housings having two cavities, it is with the scope of the invention that reservoir housing could be formed with one or more cavities in each housing.

While there have been described herein what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A method of making an integral reservoir housing for an iontophoretic drug delivery device comprising the steps of:
    providing a sheet of material containing at least one region of conductive material and at least one region of non-conductive material; said conductive and non-conductive regions forming at least one interface where said conductive and non-conductive material meet, and the sheet of material including a planar surface portion that includes a conductive surface portion and a non-conductive surface portion;
    forming a reservoir blank out of said sheet of material, said reservoir blank having at least one conductive region and at least one non-conductive region;
    forming a first cavity in said reservoir blank, said first cavity at least partially formed out of a conductive region of said reservoir blank;
    forming a second cavity in the sheet of material; and
    wherein said first cavity and said second cavity are separated by at least one region of non-conductive material.

2. The method of claim 1, wherein said second cavity is at least partially formed out of a region of conductive material of the reservoir blank, other than the regions used to form said first cavity.

3. The method of claim 2, wherein said conductive material in said sheet of material comprises a polymer.

4. The method of claim 2, comprising forming the sheet of material by extrusion.

5. The method of claim 2, comprising coextruding at least three strips of materials to form the sheet of material, the at least three strips of materials including conductive strip and nonconductive strip.

6. The method of claim 2, comprising coextruding at least two strips of materials in a coplanar manner to form the sheet of material, the at least two strips of materials including conductive strip and nonconductive strip.

7. A method of making an integral reservoir housing for an iontophoretic drug delivery device comprising the steps of:
    providing a sheet of material comprising one region of non-conductive material having a first side and a second side, said sheet of material further comprising a first and a second region of conductive material, said first conductive region disposed in contact with said first side of said non-conductive material and said second conductive region disposed in contact with said second side of said non-conductive material; said conductive and non-conductive regions forming at least one interface where said conductive and non-conductive material meet, and the sheet of material including a planar surface portion that includes a conductive surface portion and a nonconductive surface portion;
    forming a reservoir blank out of said sheet of material, said reservoir blank having at least one conductive region and at least one non-conductive region;
    forming a first cavity in said reservoir blank, said first cavity at least partially formed out of a conductive region of said reservoir blank;
    forming a second cavity in said reservoir blank; and
    wherein all conductive regions are separated from each other by non-conductive regions.

8. A method of making an integral reservoir housing for an iontophoretic drug delivery device comprising the steps of:
    providing a sheet of material comprising a first and a second separate region of conductive material, each having a first end and a second end, said conductive regions separated by a first region of non-conductive material disposed so as to be in contact with the second end of each of said regions of conductive material, said sheet of material further comprising a second and a third region of non-conductive material, wherein said second non-conductive region is disposed at the first end of said first region of conductive material and said third region of non-conductive material is disposed at said first end of said second region of conductive material; said conductive and non-conductive regions forming at least one interface where said conductive and non-conductive material meet, and the sheet of material including a planar surface portion that includes a conductive surface portion and a nonconductive surface portion;
    forming a reservoir blank out of said sheet of material, said reservoir blank having at least one conductive region and at least one non-conductive region;
    forming a first cavity in said reservoir blank, said first cavity at least partially formed out of a conductive region of said reservoir blank;
    forming a second cavity in said reservoir blank; and
    wherein all conductive regions are separated from each other by non-conductive regions.

9. A method of making an integral reservoir housing for an iontophoretic drug delivery device comprising the steps of:
    providing a sheet of material comprising one region of non-conductive material having a first side and a second side, said sheet of material further comprising a first and a second region of partially conductive material, said partially conductive material comprised of at least one region of conductive material and one region of non-conductive material, said first partially conductive region disposed at said first side of said non-conductive material and said second partially conductive region disposed at said second side of said non-conductive material, and the sheet of material including a planar surface portion that includes a conductive surface portion and a nonconductive surface portion;
    forming a reservoir blank out of said sheet of material, said reservoir blank having at least one conductive region and at least one non-conductive region;
    forming a first cavity in said reservoir blank, said first cavity at least partially formed out of a conductive region of said reservoir blank;
    forming a second cavity in said reservoir blank; and
    wherein all conductive regions are separated from each other by non-conductive regions.

10. A method of making an integral reservoir housing for an iontophoretic drug delivery device comprising the steps of:
    providing a sheet of material comprising one region of non-conductive material having a first side and a second side, said sheet of material further comprising a first and a second region of partially conductive material, said partially conductive material comprised of at least one region of conductive material and one region of non-conductive material, said first partially conductive region disposed at said first side of said non-conductive material and said second partially conductive region disposed at said second side of said nonconductive material, and the sheet of material including a planar surface portion that includes a conductive surface portion and a nonconductive surface portion;

forming a reservoir blank out of said sheet of material, said reservoir blank having at least one conductive region and at least one non-conductive region;

forming a first cavity in said reservoir blank, said first cavity being completely formed out of a conductive region of said reservoir blank;

forming a second cavity in said reservoir blank; and wherein all conductive regions are separated from each other by non-conductive regions.

11. A method of making an integral reservoir housing for an iontophoretic drug delivery device comprising the steps of:

providing a sheet of material containing at least one region of conductive material and at least one region of non-conductive material; said conductive and non-conductive regions forming at least one interface where said conductive and non-conductive material meet to result in a joint between a conductive surface portion and a nonconductive surface portion, said interface not on the same plane as said conductive surface portion or said nonconductive surface portion;

forming a reservoir blank out of said sheet of material, said reservoir blank having at least one conductive region and at least one non-conductive region;

forming a first cavity in said reservoir blank, said first cavity at least partially formed out of a portion of one of said conductive regions of said reservoir blank;

forming a second cavity in said reservoir blank; and wherein all conductive regions are separated from each other by non-conductive regions.

12. A method of making an integral reservoir housing for an iontophoretic drug delivery device comprising the steps of:

providing a sheet of material containing at least one region of conductive material and at least one region of non-conductive material; said conductive and non-conductive regions forming at least one interface where said conductive and non-conductive material meet, and the sheet of material including a planar surface portion that includes a conductive surface portion and a nonconductive surface portion;

forming a reservoir blank out of said sheet of material, said reservoir blank having at least one conductive region and at least one non-conductive region;

forming a first cavity in said reservoir blank, said first cavity at least partially formed out of a conductive region of said reservoir blank; all conductive regions being separated from each other by non-conductive regions;

forming a second cavity in said reservoir blank; and wherein said interface is liquid and vapor tight.

13. A method of making an integral reservoir housing for an iontophoretic drug delivery device comprising the steps of:

providing a sheet of material containing at least one region of conductive material and at least one region of non-conductive material; said conductive and non-conductive regions forming at least one interface where said conductive and non-conductive material meet, and the sheet of material including a planar surface portion that includes a conductive surface portion and a nonconductive surface portion;

forming a reservoir blank out of said sheet of material, said reservoir blank having at least one conductive region and at least one non-conductive region;

forming a first cavity in said reservoir blank, said first cavity at least partially formed out of a conductive region of said reservoir blank; all conductive regions being separated from each other by non-conductive regions;

forming a second cavity in said reservoir blank; and wherein said sheet of material is comprised of a polymer selected from the group consisting of polyvinyl chloride, polyethylene terephthalate glycol, polyethylene, polypropylene, polycarbonate, and acrylics.

* * * * *